United States Patent
Davison et al.

(10) Patent No.: US 7,033,369 B2
(45) Date of Patent: Apr. 25, 2006

(54) CANNULA FOR RECEIVING SURGICAL INSTRUMENTS

(75) Inventors: Thomas W. Davison, North Attleboro, MA (US); Timothy E. Taylor, Hoover, AL (US); Adam Sher, North Attleboro, MA (US)

(73) Assignee: Endius, Inc., Plainville, MA (US)

( * ) Notice: Subject to any disclaimer, the term of this patent is extended or adjusted under 35 U.S.C. 154(b) by 36 days.

(21) Appl. No.: 10/439,979

(22) Filed: May 16, 2003

(65) Prior Publication Data

US 2003/0195549 A1 Oct. 16, 2003

Related U.S. Application Data

(63) Continuation of application No. 09/772,605, filed on Jan. 30, 2001, now Pat. No. 6,800,084, which is a continuation-in-part of application No. 09/137,335, filed on Aug. 20, 1998, now Pat. No. 6,187,000.

(51) Int. Cl.
*A61F 11/00* (2006.01)

(52) U.S. Cl. .................................. 606/108; 604/104

(58) Field of Classification Search ............... 606/108, 606/191, 198, 205–210; 604/104, 105, 107, 604/108, 164.05, 192, 264
See application file for complete search history.

(56) References Cited

U.S. PATENT DOCUMENTS

| | | |
|---|---|---|
| 1,170,324 A | 2/1916 | Pomerene |
| 3,044,461 A | 7/1962 | Murdock |
| 3,503,398 A | 3/1970 | Fogarty et al. |
| 3,789,852 A | 2/1974 | Kim et al. |
| 4,449,532 A | 5/1984 | Storz |
| 4,451,256 A | 5/1984 | Weikl et al. |
| 4,545,374 A | 10/1985 | Jacobson |
| 4,573,448 A | 3/1986 | Kambin ................ 128/1 |
| 4,601,713 A | 7/1986 | Fuqua |
| 4,611,594 A * | 9/1986 | Grayhack et al. .......... 606/127 |
| 4,716,901 A | 1/1988 | Jackson et al. |
| 4,863,133 A | 9/1989 | Bonnell |
| 4,899,729 A | 2/1990 | Gill et al. |
| 4,921,478 A | 5/1990 | Solano et al. |

(Continued)

FOREIGN PATENT DOCUMENTS

| | | |
|---|---|---|
| EP | 0807415 A2 | 11/1997 |
| WO | WO 95/22285 | 8/1995 |
| WO | WO 01/54560 A2 | 8/2001 |

OTHER PUBLICATIONS

"Arthroscopic Lumbar Intervertebral Fusion" by Kambin, Adult Spine: Principles and Practice, pp. 2037–2046 (1997).

"Arthroscopic Techniques for Spinal Surgery" by Kambin, Operative Arthroscopy, Second Edition, pp. 1215–1225 (1996).

(Continued)

*Primary Examiner*—Julian W. Woo
*Assistant Examiner*—Victor Nguyen
(74) *Attorney, Agent, or Firm*—Knobbe, Martens, Olson & Bear LLP

(57) ABSTRACT

A cannula (10) receives surgical instruments (120) for performing a surgical procedure on a body (130). The cannula (10) comprises a tube structure (12) defining a passage (16) through which the surgical instruments (120) are inserted into the body (130). The tube structure (12) has a proximal end (20) and a distal end (62). The tube structure (12) includes an expandable portion (40) for enabling an increase in the cross-sectional area of the passage (16) at the distal end (62). The expandable portion (40) of the tube structure (12), when expanded, has a conical configuration.

21 Claims, 2 Drawing Sheets

U.S. PATENT DOCUMENTS

| | | | |
|---|---|---|---|
| 4,984,564 | A | 1/1991 | Yuen |
| 5,139,511 | A | 8/1992 | Gill et al. |
| 5,163,949 | A | 11/1992 | Bonutti |
| 5,190,561 | A | 3/1993 | Graber |
| 5,196,023 | A | 3/1993 | Martin |
| 5,197,971 | A | 3/1993 | Bonutti |
| 5,295,994 | A | 3/1994 | Bonutti |
| 5,312,417 | A | 5/1994 | Wilk |
| 5,313,962 | A | 5/1994 | Obenchain |
| 5,354,302 | A | 10/1994 | Ko |
| 5,370,647 | A | 12/1994 | Graber et al. |
| 5,370,659 | A | 12/1994 | Sakashita |
| 5,395,317 | A | 3/1995 | Kambin ................. 604/51 |
| 5,417,203 | A | 5/1995 | Tovey et al. |
| 5,439,464 | A | 8/1995 | Shapiro |
| 5,443,479 | A | 8/1995 | Bressi, Jr. |
| 5,454,365 | A | 10/1995 | Bonutti |
| 5,490,819 | A | 2/1996 | Nicholas et al. |
| 5,529,571 | A | 6/1996 | Daniel |
| 5,556,376 | A * | 9/1996 | Yoon ...................... 604/15 |
| 5,601,590 | A | 2/1997 | Bonutti et al. |
| 5,643,282 | A * | 7/1997 | Kieturakis ............. 606/114 |
| 5,667,520 | A | 9/1997 | Bonutti |
| 5,690,606 | A | 11/1997 | Slotman |
| 5,707,359 | A | 1/1998 | Bufalini |
| 5,762,629 | A | 6/1998 | Kambin |
| 5,782,919 | A | 7/1998 | Zdeblick et al. |
| 5,792,044 | A | 8/1998 | Foley et al. |
| 5,795,289 | A | 8/1998 | Wyttenbach |
| 5,827,319 | A | 10/1998 | Carlson et al. |
| 5,851,214 | A | 12/1998 | Larsen et al. |
| 5,902,231 | A | 5/1999 | Foley et al. |
| 5,954,635 | A | 9/1999 | Foley et al. |
| 5,961,499 | A | 10/1999 | Bonutti et al. |
| 5,976,161 | A | 11/1999 | Kirsch et al. |
| 5,997,508 | A | 12/1999 | Lunn et al. |
| 6,120,437 | A | 9/2000 | Yoon et al. |
| 6,126,671 | A | 10/2000 | Richards et al. |
| 6,152,871 | A | 11/2000 | Foley et al. |
| 6,162,236 | A | 12/2000 | Osada |
| 6,171,299 | B1 | 1/2001 | Bonutti |
| 6,175,758 | B1 | 1/2001 | Kambin ................. 600/426 |
| 6,187,000 | B1 * | 2/2001 | Davison et al. ............ 606/1 |
| 6,312,443 | B1 | 11/2001 | Stone |
| 6,338,730 | B1 | 1/2002 | Bonutti et al. |
| 6,358,266 | B1 | 3/2002 | Bonutti |
| 6,361,488 | B1 | 3/2002 | Davison et al. .......... 600/102 |
| 6,371,968 | B1 | 4/2002 | Kogasaka |
| 6,383,195 | B1 | 5/2002 | Richard |
| 6,494,893 | B1 | 12/2002 | Dubrul et al. |
| 6,524,320 | B1 * | 2/2003 | DiPoto .................. 606/108 |
| 6,530,880 | B1 | 3/2003 | Pagliuca ................. 600/102 |
| 6,530,926 | B1 | 3/2003 | Davison ................. 606/61 |
| 6,648,888 | B1 | 11/2003 | Shiuzas ................. 606/61 |
| 6,652,553 | B1 * | 11/2003 | Davison et al. .......... 606/190 |
| 2002/0002360 | A1 | 1/2002 | Orth et al. |
| 2003/0009130 | A1 | 1/2003 | Stecker et al. |
| 2003/0014068 | A1 | 1/2003 | Bonutti |
| 2003/0040656 | A1 | 2/2003 | Pagliuca et al. .......... 600/102 |
| 2003/0073998 | A1 | 4/2003 | Pagliuca et al. .......... 606/61 |
| 2003/0153911 | A1 | 8/2003 | Shiuzas ................. 606/61 |
| 2003/0153927 | A1 | 8/2003 | DiPoto et al. ........... 606/108 |
| 2003/0167058 | A1 | 9/2003 | Shiuzas ................. 606/61 |
| 2003/0236529 | A1 | 12/2003 | Shiuzas et al. .......... 606/105 |

OTHER PUBLICATIONS

"Diagnostic and Therapeutic Spinal Arthroscopy" by Kambin, Neurosurgery Clinics of North America, vol. 7, No. 1, pp. 65–76 (Jan. 1996).

"The Role of Minimally Invasive Surgery in Spinal Disorders" by Kambin, Advances in Operative Orthopaedics, vol. 3, pp. 147–171 (1995).

"Arthroscopic Microdiskectomy" by Kambin, Mount Sinai J. of Medicine, pp. 159–164 (Mar. 1991).

Ditsworth, David A., M.D., *Surg Neurol*, 49; 588–598, 1998 "Endoscopic Transforaminal Lumbar Discectomy and Reconfiguration: A Postero–lateral Approach into the Spinal Canal".

Endius Marketing Bulletin, 2002, Atavi Atraumatic Spine Fusion System "How do I decompress using Atavi System?".

Endius Marketing Bulletin, 2002, Atavi Atraumatic Spine Fusion System "Minimally Invasive Update on Danek".

Foley, Kevin T., M.D., Gupta, Sanjay K., M.D., Justis, Jeff R., B.S., Sherman, Michael C., M.S., *Neurosurg Focus*, 10: 1–8, 2001 "Percutaneous pedicle screw fixation of the lumbar spine".

Guiot, Bernard H., M.D., Khoo, Larry T., M.D., Fessler, Richard G., M.D., Ph.D., *SPINE*, 27, 4: 432–438, 2002 "A Minimally Invasive Technique for Decompression of the Lumbar Spine".

Kambin, Parviz, Publisher Unknown, Chapter 77, 1055–1066, Date Unknown "Arthroscopic Lumbar Interbody Fusion".

Kambin, Parviz, Publisher Unknown, Chapter 9:117–121, Date Unknown "Posterolateral Percutaneous Lumbar Interbody Fusion".

Medtronic Sofamor Danek, *METRx MicroEndoscopic Discectomy*, 1999 "An Evolution in Minimally Invasive Spine Surgery".

Medtronic Sofamor Danek, *METRx MicroDiscectomy System*, 2000 "The Next Step in Minimally Invasive Discectomy Utilizing The Operating Microscope".

Medtronic Sofmor Danek, *METRx Microdiscectomy Surgical Technique*, 2001 as described by: Donald L. Hilton, Jr., M.D., F.A.C.S. and Sylvain Palmer, M.D. F.A.C.S.

Medtronic Sofamor Danek, *Orthopedics Today*, 1–20, 2002 "Minimal Access Spinal Technologies".

Stauber, Martin H., M.D., Bassett, George S., M.D., *SPINE*, 19, 1:57–61, 1994 "Pedicle Screw Placement With Intraosseous Endoscopy".

Co–pending U.S. Appl. No. 10/440,231, filed May 16, 2003, titled Cannula for receiving surgical instruments, and assigned to the assignee of this application.

Co–pending U.S. Appl. No. 10/441,319, filed May 16, 2003 titled Cannula for receiving surgical instruments, and assigned to the assignee of this application.

Co–pending U.S. Appl. No. 10/440,002, filed May 16, 2003 titled Cannula for receiving surgical instruments, and assigned to the assignee of this application.

Co–pending U.S. Appl. No. 10/440,278, filed May 16, 2003 titled Cannula for receiving surgical instruments, and assigned to the assignee of this application.

Co–pending U.S. Appl. No. 10/439,385, filed May 16, 2003 titled Cannula for receiving surgical instruments, and assigned to the assignee of this application.

Co–pending U.S. Appl. No. 10/435,730, filed May 9, 2003 titled Method for performing a surgical procedure and a cannula for use in performing the surgical procedure, and assigned to the assignee of this application.

Co-pending U.S. Appl. No. 10/713,820, filed Nov. 14, 2003, titled Cannula for receiving surgical instruments, and assigned to the assignee of this application.

Co-pending U.S. Appl. No. 10/686,063, filed Oct. 15, 2003, titled Cannula for receiving surgical instruments, and assigned to the assignee of this application.

Co-pending U.S. Appl. No. 10/686,154, filed Oct. 15, 2003, titled Method of securing vertebrae, and assigned to the assignee of this application.

Co-pending U.S. Appl. No. 10/678,744, filed Oct. 2, 2003, titled Minimally invasive access device and method, and assigned to the assignee of this application.

Co-pending U.S. Appl. No. 10/658,736, filed Sep. 9, 2003, titled Methods and apparatuses for treating the spine through an access device, and assigned to the assignee of this application.

Co-pending U.S. Appl. No. 09/772,605, filed Jan. 30, 2001, titled Method for performing a surgical procedure and a cannula for use in performing the surgical procedure, and assigned to the assignee of this application.

Amendment to U.S. Appl. No. 09/772,605, filed Jan. 30, 2001, Office Action dated Oct. 31, 2003, Response to Office Action filed Feb. 2, 2004.

* cited by examiner

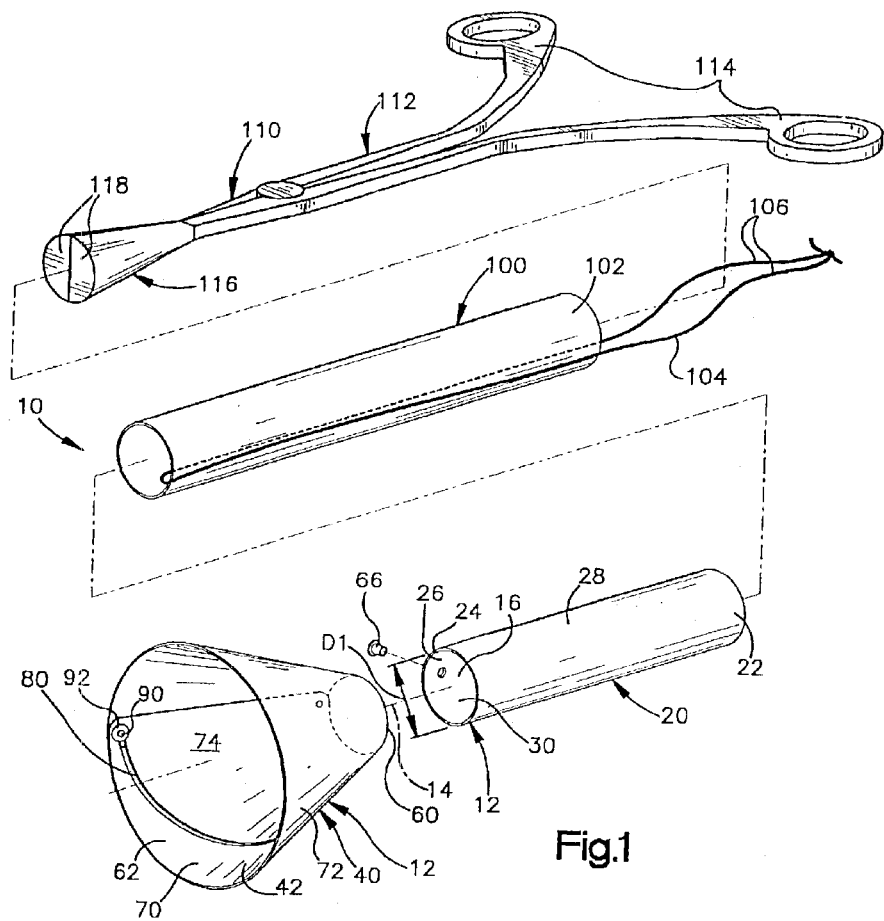
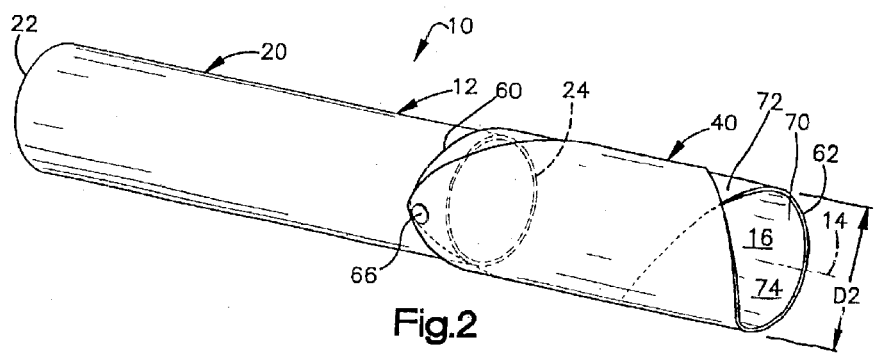

CANNULA FOR RECEIVING SURGICAL INSTRUMENTS

PRIORITY INFORMATION

This application is a continuation of U.S. application Ser. No. 09/772,605, filed Jan. 30, 2001, now U.S. Pat. No. 6,800,084, which is a continuation-in-part of U.S. application Ser. No. 09/137,335, filed Aug. 20, 1998, now U.S. Pat. No. 6,187,000.

TECHNICAL FIELD

The present invention is directed to a cannula for receiving surgical instruments for performing a surgical procedure on a body.

BACKGROUND OF THE INVENTION

Endoscopic surgical techniques allow a surgical procedure to be performed on a patient's body through a relatively small incision in the body and with a limited amount of body tissue disruption. Endoscopic surgery typically utilizes a tubular structure known as a cannula which is inserted into a small incision in the body. The cannula holds the incision open and serves as a conduit extending between the exterior of the body and the local area inside the body where the surgery is to be performed.

Due to the relatively small size of the passage into the body which is defined by the cannula, certain surgical procedures, such as posterior disectomies and procedures using steerable surgical instruments, have been difficult to perform using endoscopic techniques.

SUMMARY OF THE INVENTION

The present invention is a cannula for receiving surgical instruments for performing a surgical procedure on a body. In one embodiment, the cannula comprises a tube structure defining a passage through which the surgical instruments are inserted into the body. The tube structure has a proximal end and a distal end. The tube structure includes an expandable portion for enabling an increase in the cross-sectional area of the passage at least at the distal end.

The expandable portion of the tube structure, when expanded, has a conical configuration. The expandable portion of the tube structure includes an arcuate slot and a guide pin disposed in the arcuate slot. The guide pin is movable from a terminal end of the slot to a second terminal end of the slot to enable the cross-sectional area of the passage at the distal end to increase.

The tube structure includes first and second tubular portions attached to one another. The second tubular portion comprises the expandable portion. The first tubular portion comprises a length of stainless steel tubing, and the second tubular portion comprises an arcuate segment of stainless steel sheet stock rolled into a tubular shape.

BRIEF DESCRIPTION OF THE DRAWINGS

The foregoing and other features of the present invention will becomes apparent to one skilled in the art to which the present invention relates upon consideration of the following description of the invention with reference to the accompanying drawings, wherein:

FIG. 1 is an exploded perspective view of a surgical cannula constructed in accordance with the present invention, the cannula being shown in an expanded condition;

FIG. 2 is a perspective view of the cannula of FIG. 1 with parts removed for clarity, the cannula being shown in a contracted condition;

DETAILED DESCRIPTION OF THE PREFERRED EMBODIMENT

Figure 4:
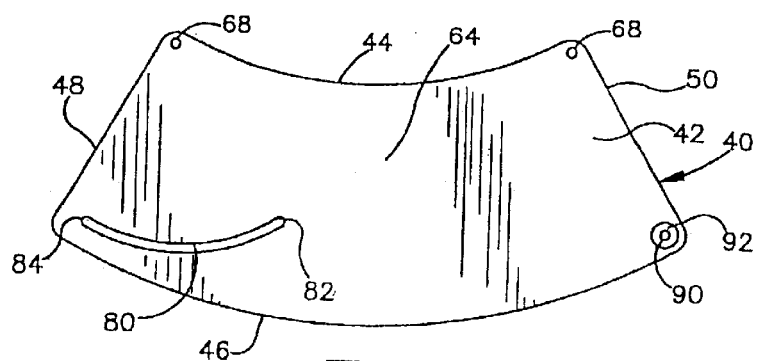
FIG. 4 is a roll out view of a part of the cannula of FIG. 1.

The present invention is directed to a cannula for receiving surgical instruments for performing a surgical procedure on the body of a patient. The present invention is applicable to a variety of surgical procedures in which endoscopic surgical techniques are used.

FIG. 1 illustrates a cannula 10 constructed according to the present invention. The cannula 10 is a tubular structure 12 centered on an axis 14. The tubular structure 12 defines a passage 16 through the cannula 10. Surgical instruments are inserted into the body during endoscopic surgery through the passage 16.

The tubular structure 12 comprises a first tubular portion 20 and a second tubular portion 40 attached to the first tubular portion. The first tubular portion 20 is preferably made of a length of stainless steel tubing, but could alternatively be made of another suitable material. The first tubular portion 20 has a proximal end 22 and a distal end 24. Parallel cylindrical inner and outer surfaces 26 and 28, respectively, extend between the ends 22, 24 of the first tubular portion 20. The inner surface 26 defines a first passage portion 30 of the passage 16 through the cannula 10. The first passage portion 30 has a diameter D1 which is preferably in the range from 10 mm to 20 mm.

The second tubular portion 40 of the tubular structure 12 is attached to the distal end 24 of the first tubular portion 20. The second tubular portion is preferably made from stainless steel, but could alternatively be made from another suitable material.

As best seen in the rollout view of FIG. 4, the second tubular portion 40 comprises an arcuate segment 42 of sheet stock. The arcuate segment 42 includes first and second arcuate edges 44 and 46, respectively, and first and second planar edges 48 and 50, respectively. The first and second planar edges 48 and 50 are rolled in an overlapping manner to form the tubular configuration of the second tubular portion 40.

When the second tubular portion 40 has been rolled into its tubular configuration, the first and second arcuate edges 44 and 46 define oppositely disposed first and second ends 60 and 62 (FIGS. 1 and 2), respectively, of the second tubular portion. The first and second ends 60 and 62 are connected by a central portion 64. The first end 60 of the second tubular portion 40 is attached to the distal end 24 of the first tubular portion 20 by a single fastener, such as a rivet 66. The rivet 66 extends through two aligned apertures 68 (FIG. 4) at the first end 60 of the second tubular portion 40. The first end 60 of the second tubular portion 40 is pivotable about the rivet 66.

The second tubular portion 40 includes parallel inner and outer surfaces 70 and 72 (FIGS. 1 and 2), respectively, extending between the first and second ends 60 and 62. The inner surface 70 defines a second passage portion 74 of the passage 16 through the cannula 10 which extends as a continuation of the first passage portion 30 in the first tubular portion 20.

An arcuate slot 80 is formed in the second tubular portion 40 and extends between the inner and outer surfaces 70 and 72 of the second tubular portion. The arcuate slot 80 extends along a curvilinear path in the central portion 64 of the second tubular portion 40 toward the second end 60 of the second tubular portion. The arcuate slot 80 has a first terminal end 82 located in the central portion 64 of the second tubular portion 40. A second terminal end 84 of the arcuate slot 80 is located adjacent the intersection of the second arcuate edge 46 and the first planar edge 48 of the arcuate segment 42.

A guide pin 90 is attached to the inner surface 70 of the second tubular portion 40 adjacent the intersection of the second arcuate edge 46 and the second planar edge 50. In the tubular configuration of the second tubular portion 40, the guide pin 90 is located in the arcuate slot 80 and is movable along the curvilinear path of the arcuate slot. A washer 92 is secured to an inner end of the guide pin 90 to retain the guide pin in the arcuate slot 80.

Figure 3:
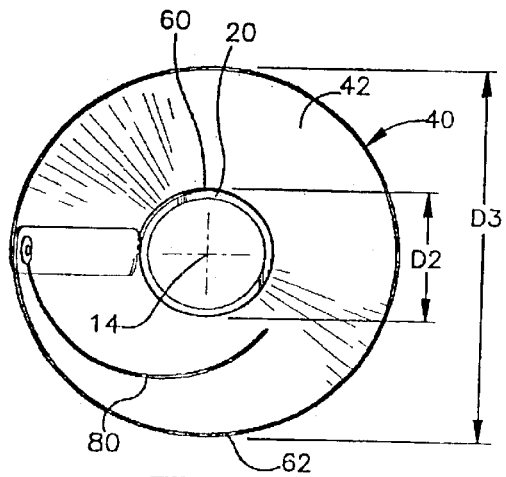
FIG. 3 is a schematic end view showing the cannula of FIG. 1 in the expanded position.

The second tubular portion 40 of the tubular structure 12 is expandable from a contracted condition shown in FIG. 2 to an expanded condition shown in FIG. 1. In the contracted condition, the guide pin 90 is located in the first terminal end 82 of the arcuate slot 80 in the second tubular portion 40 and the second passage portion 74 defined by the second tubular portion is cylindrical in shape. The second passage 74 has a generally constant diameter D2 (FIGS. 2 and 3) which is approximately equal to the diameter D1 of the first tubular portion 20. Thus, the cross-section area of the second passage portion 74 at the second end 62 of the second tubular portion 40, which is a function of the diameter D2, is approximately the same as the cross-sectional area at the first end 60 of the second tubular portion and is approximately the same as the cross-sectional area of the first passage portion 30 in the first tubular portion 20.

In the expanded condition, the guide pin 90 is located in the second terminal end 84 of the arcuate slot 80 in the second tubular portion 40 and the second tubular portion has a conical configuration. At the second end 62 of the second tubular portion 40, the second passage portion 74 has a diameter D3 (FIG. 3) which is larger than the diameter D2 of the second passage portion at the first end 60. Preferably, the diameter D3 of the second passage portion 74 at the second end 62 of the second tubular portion 40 is 40% to 80% greater than the diameter D2 of the second passage portion at the first end 60. Thus, in the expanded condition, the cross-sectional area of the second passage portion 74 at the second end 62 of the second tubular portion 40, which is a function of the diameter D3, is 40% to 80% greater than the cross-sectional area of the second passage portion at the first end 60 of the second tubular portion.

The cannula 10 includes an outer layer 100 (FIG. 1) for maintaining the second tubular portion 40 of the cannula in the contracted condition. It is contemplated that other suitable means for maintaining the second tubular portion 40 in the contracted condition could be employed. In accordance with a preferred embodiment of the present invention, the outer layer 100 comprises a section of plastic tubing 102 which is heat shrunk over both the first and second tubular portions 20 and 40 to hold the second tubular portion in the contracted condition.

In addition, a loop of nylon string 104 for tearing the heat shrink tubing 102 is wrapped around the heat shrink tubing so that it extends bath underneath and on top of the tubing. An outer end 106 of the string 104 extends beyond the tubing 102.

The cannula 10 further includes an actuatable device 110 for expanding the second tubular portion 40 from the contracted condition to the expanded condition. In accordance with a preferred embodiment of the present invention, the actuatable device 110 comprises a manually operated expansion tool 112. The expansion tool 112 resembles a common pair of scissors and has a pair of legs 114 pivotally connected to one another. The expansion tool 112 includes a frustoconical end section 116 formed by a pair of frustoconical halves 118. Each of the frustoconical halves 118 extends from a respective one of the legs 114 of the expansion tool 112. It is contemplated that other suitable means for expanding the second tubular portion 40 toward the expanded condition could be employed, such as an inflatable balloon (not shown).

During an endoscopic surgical procedure, the cannula 10 is inserted in the contracted condition into the body of a patient. The outer end 106 of the string 104 is then manually pulled on by the surgeon. Pulling on the string 104 tears the heat shrink tubing 102 which is then removed from the cannula 10 by the surgeon. With the heat shrink tubing 102 removed, the second tubular portion 40 of the cannula 10 is thereby released for expansion toward the expanded condition.

Figure 5:
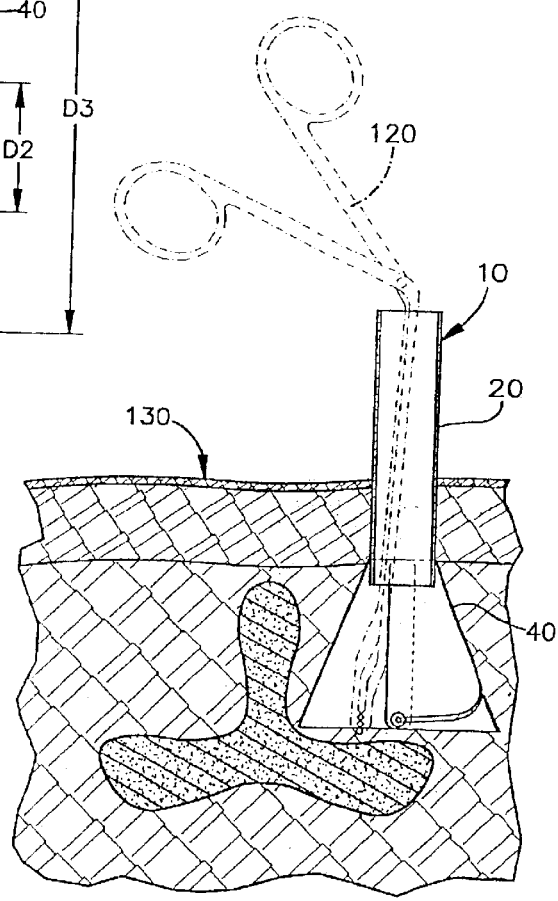
FIG. 5 is a schematic sectional view of the cannula of FIG. 1 during a surgical procedure.

Next, the expansion tool 112 is inserted into the passage 16 in the cannula 10 until the frustoconical end section 114 is located at the second end 62 of the second tubular portion 40. The legs 118 of the expansion tool 112 are manually separated, causing the frustoconical halves 118 to separate also. As the halves 118 separate, a radially outwardly directed force is exerted on the inner surface 70 of the second tubular portion 40 by the halves 118, causing the second tubular portion to expand toward the expanded condition. Under the force of the expanding expansion tool 112, the guide pin 90 slides from the first terminal end 82 of the arcuate slot 80 to the second terminal end 84 of the arcuate slot to permit the expansion of the second tubular portion 40. The expansion tool 112 can be rotated about the axis 14 to ensure that the second tubular portion 40 of the cannula 10 is completely expanded to the expanded condition. The expansion tool 112 is then collapsed and removed so that one or more surgical instruments (indicated schematically at 120 in FIG. 5) and a viewing element can be received through the cannula 10 and inserted into a patient's body 130. The expandable second tubular portion 40 of the cannula 10 provides a significantly larger working area for the surgeon inside the body 130 within the confines of the cannula.

As a result, the simultaneous use of a number of endoscopic surgical instruments, including but not limited to steerable instruments, shavers, dissectors, scissors, forceps, retractors, dilators, and video cameras, is made possible by the expandable cannula 10.

It is contemplated that the cannula 10 described herein could be the centerpiece of a endoscopic surgical kit which would include an assortment of surgical instruments designed and/or selected for use with the cannula.

From the above description of the invention, those skilled in the art will perceive improvements, changes and modifications. Such improvements, changes and modifications within the skill of the art are intended to be covered by the appended claims.

What is claimed is:

1. A system for providing minimally invasive access to the spine of a patient, said system comprising:

an elongate body having a distal end, a proximal end, an outer surface, and an inner surface, said inner surface defining a passage extending through the elongate body through which instruments can be inserted to a surgical location, said elongate body having a first configuration for insertion into the patient, and a second configuration for increasing access to the surgical location, wherein in the second configuration, the inner surface defines a cross-sectional area of the passage at a first location that is greater than a cross-sectional area of said passage at a second location, the first location being distal to the second location; and an expander comprising a first elongate member and a second elongate member pivotably coupled with the first elongate member, and a proximal end, the expander configured to be inserted into the passage and to be actuated from the proximal end such that the first and second elongate members engage the inner surface adjacent the distal end to cause opposing portions of the distal end of the elongate body to be moved transversely to increase access to the surgical location.

2. The system of claim 1, wherein the elongate body comprises rigid material extending around substantially the entire perimeter of the cross-sectional area between the first and second locations.

3. The system of claim 1, wherein the inner surface defining the passage is made of a smooth metal.

4. The system of claim 1, wherein the passage is sized to receive at least two instruments simultaneously.

5. The system of claim 1, wherein the expander comprises a pair of legs pivotally connected to one another.

6. The system of claim 1, wherein the elongate body includes an area overlap between the inner surface and outer surface, and wherein actuating the expander reduces the area of overlap.

7. The system of claim 1, wherein the elongate body includes two portions capable of pivoting relative to each other, and wherein actuating the expander causes the two portions to pivot relative to each other.

8. A system for providing minimally invasive access to the spine of a patient, said system comprising:

an elongate body having a distal end, a proximal end, an outer surface, and an inner surface, said inner surface defining a passage extending through the elongate body through which instruments can be inserted to a surgical location, said elongate body having a first configuration for insertion into the patient, and a second configuration for increasing access to the surgical location, wherein in the second configuration, the inner surface defines a cross-sectional area of the passage at a first location that is greater than a cross-sectional area of said passage at a second location, the first location being distal to the second location; and an expander comprising a first leg and a second leg pivotably coupled with the first leg, the expander configured to be actuated such that the first and second legs when actuated cause the elongate body to have the second configuration.

9. The system of claim 8, wherein the elongate body comprises rigid material extending around substantially the entire perimeter of the cross-sectional area between the first and second locations.

10. The system of claim 8, wherein the inner surface defining the passage is made of a smooth metal.

11. The system of claim 8, wherein the passage is sized to receive at least two instruments simultaneously.

12. The system of claim 8, wherein the elongate body includes an area overlap between the inner surface and outer surface, and wherein actuating the expander reduces the area of overlap.

13. The system of claim 8, wherein the elongate body includes two portions capable of pivoting relative to each other.

14. The system of claim 13, wherein the two portion of the elongate body are configured to be pivoted by actuating the expander.

15. The system of claim 8, wherein the expander is configured to be inserted into the passage and to engage the inner surface of the elongate body when actuated.

16. A system for providing minimally invasive access to the spine of a patient, said system comprising:

an elongate body having a distal end, a proximal end, an outer surface and an inner surface, said inner surface defining a passage extending through the elongate body through which instruments can be inserted to a surgical location, said elongate body having a first configuration for insertion into the patient, and a second configuration for providing access to the surgical location, wherein in the second configuration, the inner surface defines a cross-sectional area of the passage at a first location that is greater than a cross-sectional area of said passage at a second location, the first location being distal to the second location; and an expander comprising a first leg and a second leg pivotably coupled with the first leg, the expander configured to be actuated to cause the elongate body to have the second configuration, the expander further configured to be engagable and disengageble from the elongate body;

wherein the elongate body maintains the second configuration when the expander is disengaged therefrom.

17. The system of claim 16, wherein the passage is sized to receive at least two instruments simultaneously.

18. The system of claim 16, wherein the elongate body includes an area overlap between the inner surface and outer surface, and wherein actuating the expander reduces the area of overlap.

19. The system of claim 16, wherein the elongate body includes two portions capable of pivoting relative to each other.

20. The system of claim 19, wherein the two portion of the elongate body are configured to be pivoted by actuating the expander.

21. The system of claim 16, wherein the expander is configured to be inserted into the passage and to engage the inner surface of the elongate body when actuated.

* * * * *

UNITED STATES PATENT AND TRADEMARK OFFICE
CERTIFICATE OF CORRECTION

PATENT NO. : 7,033,369 B2
APPLICATION NO. : 10/439979
DATED : April 25, 2006
INVENTOR(S) : Thomas Davison et al.

It is certified that error appears in the above-identified patent and that said Letters Patent is hereby corrected as shown below:

Page 2; U.S. Patent Documents; Line 50:
   After "6,494,893" please delete "B1" and insert therefore, --B2--

Page 2; U.S. Patent Documents; Line 51:
   After "6,524,320" please delete "B1" and insert therefore, --B2--

Page 2; U.S. Patent Documents; Line 52:
   After "6,530,880" please delete "B1" and insert therefore, --B2--

Page 2; U.S. Patent Documents; Line 53:
   After "6,530,926" please delete "B1" and insert therefore, --B2--

Page 2; U.S. Patent Documents; Line 54:
   After "11/2003" please delete "Shiuzas" and insert therefore, --Shluzas--

Page 2; U.S. Patent Documents; Line 55:
   After "6,652,553" please delete "B1" and insert therefore, --B2--

Page 2; U.S. Patent Documents; Line 61:
   After "8/2003" please delete "Shiuzas" and insert therefore, --Shluzas--

Page 2; U.S. Patent Documents; Line 63:
   After "9/2003" please delete "Shiuzas" and insert therefore, --Shluzas--

Page 2; U.S. Patent Documents; Line 64:
   After "12/2003" please delete "Shiuzas et al." and insert therefore,
   --Shluzas et al.--

Page 2; Other Publications; Col. 2; Line 35:
   Please delete "Sofmor" and insert therefore, --Sofamor--

Page 2; Other Publications; Col. 2; Line 37:
   Please delete "M.D." and insert therefore, --M.D.,--

Page 2; Other Publications; Col. 2; Line 46:
   After "2003" please add --,--

Page 2; Other Publications; Col. 2; Line 49:
   After "2003" please add --,--

UNITED STATES PATENT AND TRADEMARK OFFICE
CERTIFICATE OF CORRECTION

PATENT NO. : 7,033,369 B2
APPLICATION NO. : 10/439979
DATED : April 25, 2006
INVENTOR(S) : Thomas Davison et al.

It is certified that error appears in the above-identified patent and that said Letters Patent is hereby corrected as shown below:

Page 2; Other Publications; Col. 2; Line 52:
　　After "2003" please add --,--

Page 2; Other Publications; Col. 2; Line 55:
　　After "2003" please add --,--

Page 2; Other Publications; Col. 2; Line 58:
　　After "2003" please add --,--

Column 1; Line 30:
　　Please delete "disectomies" and insert therefore, --discectomies--

Column 1; Line 53:
　　Please delete "tubing," and insert therefore, --tubing--

Column 3; Line 29:
　　Please delete "cross-section" and insert therefore, --cross-sectional--

Column 3; Line 65:
　　Please delete "bath" and insert therefore --both--

Column 4; Line 55:
　　Please delete "a" and insert therefore, --an--

Column 6; Line 38 (Claim 16):
　　Please delete "engagable" and insert therefore, --engageable--

UNITED STATES PATENT AND TRADEMARK OFFICE
CERTIFICATE OF CORRECTION

PATENT NO. : 7,033,369 B2
APPLICATION NO. : 10/439979
DATED : April 25, 2006
INVENTOR(S) : Thomas Davison et al.

It is certified that error appears in the above-identified patent and that said Letters Patent is hereby corrected as shown below:

Column 6; Line 38 (Claim 16):
    Please delete "disengageble" and insert therefore, --disengageable--

Signed and Sealed this

Nineteenth Day of December, 2006

JON W. DUDAS
*Director of the United States Patent and Trademark Office*